United States Patent [19]
Iosif

[11] Patent Number: 5,428,871
[45] Date of Patent: Jul. 4, 1995

[54] CLAMP FOR ELASTOMERIC BAGS

[75] Inventor: Mario C. Iosif, Clark, N.J.

[73] Assignee: C. R. Bard, Inc., Murray Hill, N.J.

[21] Appl. No.: 139,023

[22] Filed: Oct. 21, 1993

[51] Int. Cl.⁶ .................................................. B65D 77/00
[52] U.S. Cl. .................................. 24/30.5 R; 24/30.5 P;
24/543; 606/120
[58] Field of Search ................ 24/543, 30.5 R, 30.5 P,
24/507, 487; 251/10; 604/227, 335; 606/120

[56] References Cited

U.S. PATENT DOCUMENTS

| | | | |
|---|---|---|---|
| 3,106,919 | 10/1963 | Churchville | 606/120 |
| 3,247,852 | 4/1966 | Schneider | 606/120 |
| 3,461,876 | 8/1969 | Miller, Jr. | 251/10 |
| 3,571,861 | 3/1971 | Olson . | |
| 3,854,482 | 12/1974 | Laugherty et al. | 606/120 |
| 3,874,042 | 4/1975 | Eddleman et al. | 251/10 |
| 4,097,967 | 7/1978 | Conner, Jr. . | |
| 4,275,485 | 6/1981 | Hutchison | 24/30.5 P |
| 4,296,529 | 10/1981 | Brown | 24/30.5 P |
| 4,460,359 | 7/1984 | Fenton | 24/30.5 P |
| 4,551,888 | 11/1985 | Beecher . | |
| 4,656,697 | 4/1987 | Naslund . | |
| 4,811,465 | 3/1989 | Folkmar . | |
| 4,834,730 | 5/1989 | Holtermann et al. . | |
| 4,866,818 | 9/1989 | Thompson . | |
| 4,887,335 | 12/1989 | Folkmar . | |
| 4,960,521 | 10/1990 | Keller . | |
| 4,983,173 | 1/1991 | Patience et al. . | |
| 5,000,747 | 3/1991 | Cardo et al. . | |
| 5,050,272 | 9/1991 | Robinson et al. . | |
| 5,079,806 | 1/1992 | Allen . | |
| 5,115,542 | 5/1992 | Gehres | 24/543 |
| 5,123,146 | 6/1992 | Olson . | |
| 5,125,133 | 6/1992 | Morrison . | |
| 5,226,892 | 7/1993 | Boswell | 24/543 |

Primary Examiner—Victor N. Sakran
Attorney, Agent, or Firm—Dennison, Meserole, Pollack & Scheiner

[57] ABSTRACT

A clamp for thin-walled elastomeric waste collection bags including a molded thermoplastic body with opposed elongate clamping legs. Each leg mounts an elongate rigid blade having a linear edge. The linear edges of the blades align to opposite sides of the bag material as the clamp is closed thereon.

14 Claims, 1 Drawing Sheet

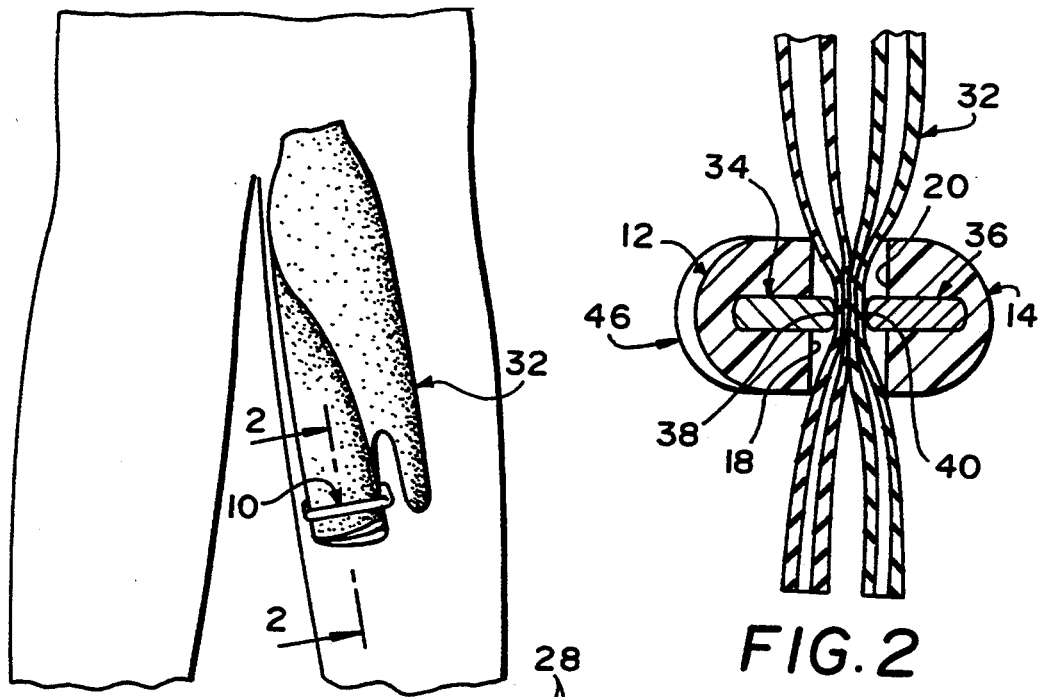
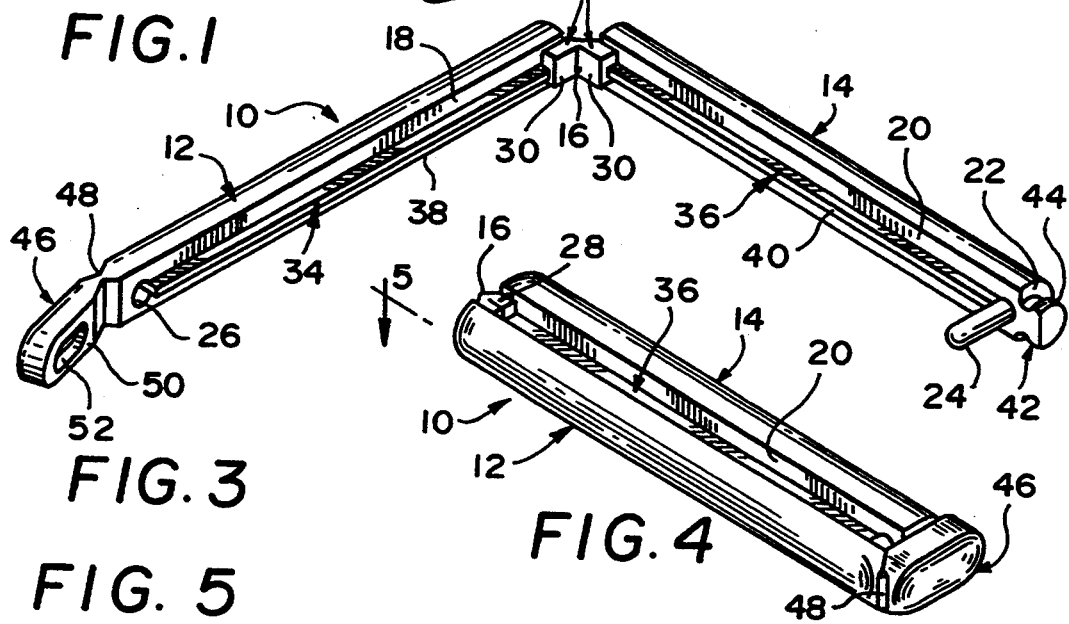
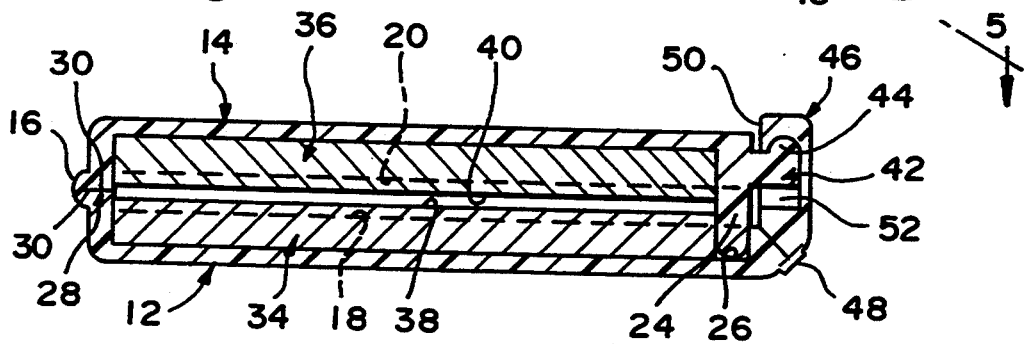

CLAMP FOR ELASTOMERIC BAGS

BACKGROUND OF THE INVENTION

Elastomeric bags, particularly of the type used to collect body wastes such as fecal matter, will, if reusable, include a bag emptying opening formed at the lower end thereof, preferably in a spout-like depending portion. This opening is sealed by a clamp which allows opening of the bag for emptying of the contents, and a resealing of the bag for continued use.

A variety of such clamps have been proposed wherein the clamp is molded of an appropriate plastic and includes a pair of elongate legs joined by a living hinge at one end and including some form of releasable latch means at the other end, the bag, about the opening, being clamped between the legs.

Examples of such clamps will be noted in U.S. Pat. Nos. 4,551,888; 4,834,730 and 5,125,133.

The formation of such clamps of plastic, that is a thermoplastic or synthetic resinous material, is particularly desirable in that the clamp can be inexpensively molded as a one-piece item with an integral hinge and latch. The clamps so formed are usually intended for reuse.

However, elastomeric materials of the type used in the formation of thin-walled fecal collection bags and the like give rise to special problems. For example, such elastomeric bag materials, by their very nature, provide a substantial resistance to clamping forces. Because of this resistance or reacting force, the clamp itself must be sufficiently stiff so as to avoid any flexure as might allow leakage. The known clamps have not been noted as being of such stiffness or rigidity and are not, particularly after repeated use, considered very effective in retaining a seal.

In one form of known clamp, a grooved or female locking part is provided within which the elastomeric material is clamped by a male member. However, because of the nature of the elastomeric materials, it is difficult to press the materials into and in conformance with the cavity of the female locking part. Further, most elastomers have a high coefficient of friction which causes "pulling" problems when they are forced into a cavity.

Thus, while molded one-piece clamps include the advantages of being inexpensive to fabricate and capable of being reused several times, the actual sealing capabilities of the known clamps, particularly as with regard to elastomeric materials of the type used in human waste collection bags, are less than completely effective.

SUMMARY OF THE INVENTION

The clamp comprising the present invention includes all of the desirable features of known clamps in that it comprises an inexpensive molded body wherein the two clamping legs are interconnected by a hinge, preferably an integral living hinge, at one end and by a releasable molded latch assembly at the opposite end.

However, the improved clamp of the invention, to accommodate the nature of the elastic materials of the bags, differs from conventional clamps by providing a symmetrical or identical sealing effect by both of the clamping legs to both sides of and against both sides of the material being clamped. This sealing action effects a positive male part-against male part action as opposed to the heretofore actions of such collection bag clamps relying on an opposed groove and male part or blade, a male part and an opposed flat surface, and the like.

The clamp of the invention, rather than attempting to conform the elastomeric material to a cavity or female part, or merely press the layers of material in intimate contact with each other, specifically penetrates the wall thickness. That is, in addition to bringing the walls in intimate contact with each other, the clamp also, through opposed line contact, compresses the wall thicknesses. Thus any tendency for relative movement of the clamped walls, or "pulling" problems, which are normally inherent because of the nature of the elastomeric materials, are avoided.

The advantages of the invention are achieved by providing the opposed clamping legs with elongate stiff or non-flexing blades, preferably of metal. Such blades, for example of stainless steel, form opposed male parts with linear outer edges which, in the closed position of the clamp, are in a common plane and extend in slightly spaced parallel relation to each other.

The provision of such blades eliminates the problems associated with the inherent flexibility of the plastic material of the prior art clamps, while at the same time retaining the advantages thereof with regard to an inexpensive molded construction with integral hinges and latches.

The outer or exposed edges of the blades are slightly rounded to avoid any tendency to cut or otherwise damage the bag material. Further, the transverse spacing between these opposed parallel edges in the closed clamp is to be substantially less than the combined thicknesses of the bag walls to be clamped thereby. In this manner, the walls are both brought into intimate engagement with each other and individually and significantly compressed, without cutting, by the blade edges to avoid any creeping or relative movement between the bag layers.

Other features, objects and advantages of the invention will become apparent from the more detailed discussion of the invention presented hereinafter.

BRIEF DESCRIPTION OF THE DRAWINGS

FIG. 1 schematically illustrates a portion of a human body with a waste collection bag and the clamp of the invention mounted to and sealing the waste collection bag;

FIG. 2 is an enlarged cross-sectional detail through the closed clamp taken substantially on a plane passing along line 2—2 in FIG. 1;

FIG. 3 is a perspective view of the clamp in its open position;

FIG. 4 is a perspective view of the closed clamp; and

FIG. 5 is a longitudinal cross-sectional view through the closed clamp taken substantially on a plane passing along line 5—5 in FIG. 4.

DESCRIPTION OF PREFERRED EMBODIMENT

Referring now more specifically to the drawings, the clamp 10 includes a molded body of plastic, that is synthetic resinous or thermoplastic material, comprising a pair of elongate legs 12 and 14 joined at first inner ends thereof by a hinge, preferably an integral living hinge 16. Each of the legs 12 and 14 has a planar inner face or surface, 18 and 20 respectively, along at least substantially the full length thereof.

The leg 14, adjacent the second outer end 22 thereof, has an integral guide pin 24 projecting perpendicular from the planar inner face 20 thereof on the longitudinal center line of the face. A corresponding socket 26, within the leg 12 and opening inwardly through the inner face 18 thereof, is similarly located and positioned to receive the guide pin 24 as the legs 12 and 14 are closed on each other. The length of the guide pin 24 and the depth of the socket 26 are such whereby with the guide pin fully seated, as illustrated in FIG. 5, the opposed leg faces 18 and 20 are positioned in spaced parallel relation to each other with the legs 12 and 14 transversely aligned. The relative sizes of the guide pin 24 and socket 26 are such as to provide for a snug interfit whereby lateral and longitudinal shifting between the legs is precluded.

In order to assist in maintaining the parallel relationship between the inner surfaces 18 and 20 for the full length of the overlying coextensive legs, each leg, adjacent the hinged inner end thereof, includes an integral abutment block 28 having a planar inner face 30 which parallels the corresponding inner surface 18 or 20 and which, in the closed clamp as in FIG. 5, abut each other as the guide pin 24 fully seats within the socket 26.

The actual clamping force to be applied to the elastomeric material of the bag 32 is effected by a pair of opposed rigid blades 34 and 36, preferably metal, and particularly stainless steel. The blades 34 and 36 are permanently affixed to the legs 12 and 14 respectively, with the legs preferably molded to the blades.

The blade 34 extends along the longitudinal center line of the leg 12 and projects from the planar inner surface 18 thereof from the inner end abutment block 28 to the pin-receiving socket 26. The blade 36, similarly along the longitudinal center line of leg 14, projects from the inner surface 20 thereof and extends longitudinally between the inner end abutment block 28 and the guide pin 24.

The blades 34 and 36 terminate in linear slightly rounded inner edges 38 and 40 respectively. These inner edges 38 and 40 are of a height, from the corresponding inner leg surfaces 18 and 20, slightly less than that of the corresponding abutment blocks 28 whereby, in the closed position of the clamp as in FIG. 5, the inner edges 38 and 40 are in a slightly spaced, laterally aligned, parallel relation to each other. This spacing, noting the sectional detail of FIG. 2, is substantially less than the combined thicknesses of the layers of material of the bag 32 which are to be clamped whereby the layers of material are not only brought into close engagement with each other, but are actually individually compressed to a substantial degree.

In order to lock the clamp in its closed position, a latch assembly is provided. The latch assembly comprises a longitudinally extending lug 42 projecting integrally from the free outer end 22 of leg 14 and including an enlarged bulbous or undercut head portion 44 thereon outward of the leg end 22. The latch assembly also includes an elongate latch 46 hinged to the free second or outer end of the leg 12 by hinge 48, preferably an integral living hinge, for selective movement, in the closed position of the clamp, into locking engagement with the lug 42. The latch 46 includes an inner face 50 having an undercut socket or recess 52 therein which is so oriented as to, upon alignment with the lug 42, snap lock over the bulbous or enlarged head 44 thereof. It will be noted that the latch 46 is turned at approximately right angles to the leg 12 when engaged with the lug 42. As such, any force of the compressed bag material acting against the clamping force will merely enhance the latch and lug engagement. Disengagement of the latch will require a positive manual force acting laterally against the latch 46 longitudinally outward of the closed legs. In this manner, any accidental disengagement of the clip is precluded. It will of course be appreciated that the specific configuration of the recess 52 and lug 42, and particularly the undercut portions thereof, are such as to, through the inherent flexibility of the material of the plastic body, snap lock and snap release upon appropriate manual pressure. Further, and noting FIG. 5, the latch interlock is effected when the legs are in their closed position with the inner edges 38 and 40 of the blades parallel and with the guide pin 24 and abutment faces 30 fully seated.

Referring again to FIG. 2, in the closed and locked clamp, the inner clamping edges 38 and 40 of the rigid blades 34 and 36, are co-planar or in direct opposed alignment to provide coextensive male or line engagement at directly opposed lines along the length of material being clamped. This alignment is facilitated by the socket receive guide pin 24. Further, the transverse distance between these edges 38 and 40, being substantially less than the combined thicknesses of the material of the bag being clamped, effect not only an intimate engagement of the material layers together, but also an actual deforming of the walls and a substantial reduction of the wall thicknesses along the narrow line of contact. This effect is assured by the stiff or rigid nature of the blades which preclude any flexing of the clamping blades or blade edges, even after repeated uses of the clamp. It is also to be recognized that this line clamping and compressing of the bag material, with no flexing of the blades or blade edges being possible, eliminates any tendency for the elastomeric layers to creep or otherwise shift relative to each other as might reduce the sealing effect.

The combination of such blades, preferably metal, with a thermoplastic material body, in the manner described, is of particular significance in providing for the desired positive sealing effect achieved by the blades while retaining the desirable features of a thermoplastic body, including a molded unitary construction, hinges, integral latches, and the like.

Finally, the actual number of layers of bag material to be clamped will depend on the particular nature of the bag. For example, in bag 32 of FIGS. 1 and 2, the bag is folded before clamping, thus forming four layers. The number of layers will in turn generally dictate the size of clamp used and the preferred spacing between the clamping edges 38 and 40 in the closed clamp.

The foregoing described embodiment is considered illustrative of the invention, and as other embodiments incorporating the inventive features may occur to those skilled in the art, the disclosed embodiment is not to be considered as a limitation on the scope of the invention. Rather, the invention is to only be limited by the scope of the claims following hereinafter.

I claim:

1. A clamp for closing elastomeric bags, said clamp comprising first and second elongate legs of a molded synthetic resin material, each leg having a first end and a second end, a living hinge integrally joining said first ends for selective movement of said legs between a closed position wherein said legs extend in overlying coextensive relation to each other and an open position wherein said legs diverge from each other outward of said hinge; each of said legs having an inner surface which, in said closed position, is in facing relation to the inner surface of the other of said legs, and a pair of separated elongate rigid, non-flexing, clamping blades, one blade fixed to each leg and extending longitudinally along and centrally of the inner surface thereof, each blade projecting from the corresponding inner surface and terminating in a linear edge, said blades, in said closed position of said legs, being substantially coplanar and having said edges in opposed adjacent parallel relation to each other and spaced a distance substantially less than a predetermined combined thickness of overlying portions of a bag wall received between said legs for an intimate engagement of said overlying bag wall portions with each other and a compression of said wall portions to thickness less than the predetermined combined thickness of said overlying bag wall portions.

2. The clamp of claim 1 wherein said blades are of metal.

3. The clamp of claim 2 wherein said legs are molded about said metal blades.

4. The clamp of claim 3 including a guide pin on said first leg remote from said living hinge and projecting from said inner surface of said first leg, a socket in said second leg opening through said inner surface of said second leg and positioned an equal distance from said living hinge as said guide pin for engagement of said guide pin in said socket upon movement of said legs to said closed position.

5. The clamp of claim 4 including abutment means on said legs adjacent said living hinge for engaging upon movement of said legs to said closed position and for retaining said legs against movement toward each other beyond said closed position.

6. The clamp of claim 5 including latch means for releasably locking said legs in said closed position, said latch means comprising a lug integral with and extending longitudinally beyond said second end of one of said legs, and a latch pivotally joined to said second end of a second one of said legs by a living hinge, said latch having an inner face with a socket therein, said latch being pivotal between an open position outward of said lug and a latched position extending laterally from the leg to which it is joined with said lug received in said latch socket, said lug and latch socket having cooperating snap-lock means for releasable locking said lug in said latch socket.

7. The clamp of claim 2 wherein said metal blades are of steel.

8. For use in releasably closing elastomeric bags of a predetermined, resiliently compressible, wall thickness; a releasable clamp, said clamp comprising a body of molded plastic including first and second elongate legs having first ends joined by a hinge for selective movement between an open position, wherein said legs are spread for introduction of overlying portions of a bag wall therebetween for subsequent compressible clamping, said overlying wall portions being of a predetermined combined thickness, and a closed position wherein said legs are in parallel closely spaced relation to each other for clamping the introduced overlying bag wall portions therebetween, each of said legs having a separated rigid blade mounted thereon and extending longitudinally therealong, each blade, along the length thereof, extending outward of the corresponding leg and having a rigid linear clamping edge, said edges, in said closed position, extending in adjacent parallel and in spaced relation to each other a distance substantially less than the predetermined combined thickness of overlying bag wall portions received between said legs for an intimate engagement of said overlying bag wall portions with each other and a compression of said wall portions to a thickness less than the predetermined combined thickness of said overlying bag wall portions.

9. The clamp of claim 8 wherein said hinge is a living hinge integrally joining said first ends, and said rigid blades are non-flexing and of metal, said metal blades being embedded within said legs with said legs molded about said metal blades.

10. The clamp of claim 9 wherein said blades are of stainless steel, and said body is unitary.

11. The clamp of claim 9 wherein said outer clamping edge of each blade is non-piercing relative to the overlying wall portions to be clamped.

12. The clamp of claim 8 including guide means comprising a guide pin on said first leg remote from said hinge and projecting toward said second leg, a socket in said second leg opening toward said first leg and positioned an equal distance from said hinge as said guide pin for engagement of said guide pin in said leg socket upon movement of said legs to said closed position.

13. The clamp of claim 12 wherein said legs include second ends, and latch means on said second ends for releasably locking said legs in said closed position, said latch means comprising a lug integral with and extending longitudinally beyond said second end of said first leg, and a latch pivotally joined to said second end of said second leg by a hinge, said latch having an inner face with a socket therein, said latch being pivotal between an open position outward of said lug and a latched position extending laterally from said second leg and receiving said lug in said latch socket, said lug and latch socket having cooperating snap-lock means for releasable locking of said lug in said latch socket.

14. The clamp of claim 8 wherein said outer clamping edge of each blase is non-piercing relative to the overlying wall portions to be clamped.

* * * * *

UNITED STATES PATENT AND TRADEMARK OFFICE
CERTIFICATE OF CORRECTION

PATENT NO. : 5,428,871
DATED : July 4, 1995
INVENTOR(S) : Mario C. IOSIF

It is certified that error appears in the above-indentified patent and that said Letters Patent is hereby corrected as shown below:

Column 5, line 2, "separated" should read --separate--.

Column 6, line 8, "separated" should read --separate--.

Column 6, line 51, "blase" should read --blade--.

Signed and Sealed this

Twenty-second Day of August, 1995

*Attest:*

BRUCE LEHMAN

*Attesting Officer*    Commissioner of Patents and Trademarks